(12) United States Patent
Keri et al.

(10) Patent No.: US 6,521,762 B2
(45) Date of Patent: Feb. 18, 2003

(54) PROCESS FOR PURIFYING LOVASTATIN AND SIMVASTATIN WITH REDUCED LEVELS OF DIMERIC IMPURITIES

(75) Inventors: Vilmos Keri; Ilona Forgas, both of Debrecen (HU)

(73) Assignee: Biogal Gyógyszergyar Rt., Debrecen (HU)

(*) Notice: Subject to any disclaimer, the term of this patent is extended or adjusted under 35 U.S.C. 154(b) by 0 days.

(21) Appl. No.: 09/793,946

(22) Filed: Feb. 27, 2001

(65) Prior Publication Data

US 2002/0002288 A1 Jan. 3, 2002

Related U.S. Application Data

(60) Provisional application No. 60/186,868, filed on Mar. 3, 2000.

(51) Int. Cl.[7] .............................................. C07D 309/30
(52) U.S. Cl. ........................................................ 549/292
(58) Field of Search ............................................ 549/292

(56) References Cited

U.S. PATENT DOCUMENTS

| | | | |
|---|---|---|---|
| 4,294,846 A | 10/1981 | Albers-Schonberg et al. | 424/279 |
| 4,294,926 A | 10/1981 | Monaghan et al. | 435/125 |
| 4,319,039 A | 3/1982 | Albers-Schonberg | 560/256 |
| 4,342,767 A | 8/1982 | Albers-Schonberg et al. | 424/250 |
| 4,420,491 A | 12/1983 | Albers-Schonberg et al. | 424/311 |
| 4,444,784 A | 4/1984 | Hoffman et al. | 424/279 |
| 4,582,915 A | 4/1986 | Sleteinger et al. | 549/292 |
| 4,820,850 A | 4/1989 | Verhoeven et al. | 549/292 |
| 4,916,239 A | 4/1990 | Treiber | 549/292 |
| 5,917,058 A | 6/1999 | Kumar et al. | 549/292 |
| 5,939,564 A | 8/1999 | Kumar et al. | 549/292 |
| 6,380,401 B1 | 4/2002 | McManus et al. | 549/292 |

FOREIGN PATENT DOCUMENTS

| | | |
|---|---|---|
| CA | 2129416 | 2/1995 |
| DE | 44 02 591 A1 | 10/1994 |
| GB | 2 046 737 | 11/1980 |
| HU | 208 997 | 2/1994 |
| WO | WO 92/16276 | 10/1992 |
| WO | WO 97/20834 | 6/1997 |
| WO | WO 99/42601 | 8/1999 |
| WO | WO 00/17182 | 3/2000 |
| WO | WO 01/30773 | 5/2001 |

*Primary Examiner*—Amelia Owens
(74) *Attorney, Agent, or Firm*—Kenyon & Kenyon

(57) ABSTRACT

A process reducing the levels of dimeric impurities in a statin to less than 0.08% by treatment of a statin containing more than 0.08% dimeric impurities with a mild base in a suitable solvent mixture.

19 Claims, No Drawings

PROCESS FOR PURIFYING LOVASTATIN AND SIMVASTATIN WITH REDUCED LEVELS OF DIMERIC IMPURITIES

CROSS-REFERENCE TO RELATED APPLICATIONS

This application claims the benefit of U.S. provisional application Ser. No. 60/186,868, filed Mar. 3, 2000, the content of which is incorporated herein by reference.

FIELD OF THE INVENTION

The invention relates to a process of purifying Lovastatin or Simvastatin, which reduces the level of dimeric impurities in the resulting product.

BACKGROUND OF THE INVENTION

Lovastatin and its analogs, e.g. simvastatin, are potent antihyper-cholesterolemic agents that function by limiting cholesterol biosynthesis. Lovastatin is one of the most important known cholesterol lowering agents. Lovastatin (CAS Registry No. 75330-75-5) is also known as mevinolin or monacolin K and is chemically known as: β,β-dihydroxy-7-[1,2,6,7,8,8a-hexahydro-2,6-dimethyl-8-(2-methyl-butyryloxy)-1-napthalen-1-yl]-heptanoic acid β-lactone of the formula:

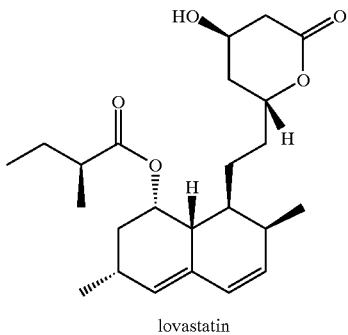

lovastatin

Lovastatin, is one member of a class of compounds, which are referred to generally as statins, are known to exist in open ring hydroxy acid and also in lactone form. The lactone form of Lovastatin is shown above.

Lovastatin and its analogs inhibit the enzyme 3-hydroxy-3-methyl-glutarylcoenzyme A reductase ("HMG-CoA reductase"). HMG-CoA reductase catalyzes the formation of mevalonic acid, an early intermediate of cholesterol biosynthesis. Lovastatin is specifically advantageous because, as a result of its application, biosynthetic intermediates that have a toxic steroid skeleton, formed at a later stage of biosynthesis fail to accumulate. Lovastatin also increases the number of LDL-receptors at the surface of the cell membrane, which remove the LDL cholesterol circulating in the blood, thereby inducing the lowering of blood plasma cholesterol level.

Lovastatin is routinely produced via fermentation. GB 2,046,737 discloses that Lovastatin can be produced by some strains belonging to the Monascus genus, e.g., by *M. ruber* 1005 cultivated between 7° and 40° C. As a culture medium, an aqueous solution of glucose, peptone, corn steep liquor and ammonium chloride was used. The fermentation was carried out for 10 days in aerobic conditions, and 87 mg Lovastatin was obtained from the filtrate of 5 liters of broth.

U.S. Pat. No. 4,294,926 discloses the biosynthesis of Lovastatin preferably by the application of microorganisms under the deposited numbers ATCC 20541 or 20542 belonging to the *Aspergillus terreus* species on a culture medium containing carbohydrates, e.g., glucose, fructose, maltose, as carbon source; nitrogen sources, e.g., yeast, hydrolyzed yeast, hydrolyzed casein, corn steep liquor, and mineral salts, e.g., calcium carbonate, magnesium sulfate, cobalt, iron, and manganese salts at a temperature of 20–37° C. Similar procedures are described in U.S. Pat. Nos. 4,420,491; 4,342,767; 4,319,039 and 4,294,846 where the fermentations are carried out for 3–5 days on media containing 1–6% carbohydrates and 0.2–6% nitrogen sources.

German Patent No. 4,402,591 discloses biosynthesis of Lovastatin by microorganisms belonging to the Pleurotus genus, e.g., *P. ostreatus, P. sapidus* and *P. saca*, at 25–35° C. during 7–14 days cultivation time on surface or submerged cultures.

Canadian Patent No. 2,129,416 discloses the preparation of Lovastatin with a microorganism belonging to the Coniothyrium genus, e.g., under the deposited number *Coniothyrium fuckelii* ATCC 74227 on a culture medium containing 3–15% glucose, 0.5–4% peptone, 0.5–5% amylase, 0.2–1% ammonium sulphate, 0.01–0.1% magnesium sulphate, 0.05–0.2% antifoaming agent, 0.2–1.5% L-isoleucine, 0.2–1.5% L-aspartic acid in the pH range of 5–6. According to the examples, the active ingredient concentration of the broth was within 19–430 mg/liter.

Hungarian Patent No. HU 208,997 discloses the application of the holotype strain *Aspergillus obscurus* numbered as MV-1, deposited under the number NCAIM(P)F 001189. The fermentation is preferably carried out on a medium containing yeast extract and/or peptone and/or casein as nitrogen source(s) and glucose and/or maltose or sucrose as carbon source(s). The activity of the broth at the end of the laboratory scale cultivation is between 400–850 mg/liter.

Simvastatin is a synthetic analog of Lovastatin, wherein the 8-acyl moiety is 2,2-dimethylbutyryl. Simvastatin is an even more potent HMG-CoA reductase inhibitor than Lovastatin. Simvastatin is chemically designated as 2,2-dimethylbutanoic acid (4R,6R)-6-[2[1S,2S, 6R,8S,8aR)-1,2, 6,7,8,8a-hexahydro-2,6-dimethyl-1-[2-(tetrahydro-4-hydroxy-6-oxo-2H-pyran-2-yl)ethyl]-1-napthalenyl ester (CAS Registry No. 79902-63-9). The chemical structure of Simvastatin is:

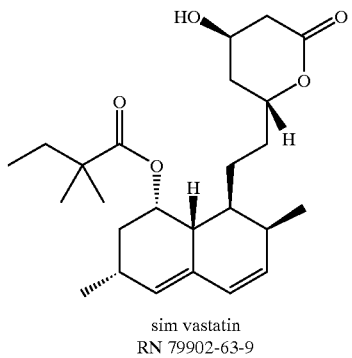

sim vastatin
RN 79902-63-9

Simvastatin is now commercially available as ZOCOR® in some markets. The preparation of Simvastatin was originally described in U.S. Pat. No. 4,444,784. The process involves deacylation of Lovastatin followed by a subsequent acylation with the 2,2-dimethylbutyryl moiety. Simvastatin has also been prepared by the alpha alkylation of the Lovastatin ester moiety as described in U.S. Pat. Nos. 4,582,915 and 4,820,850.

After the fermentation is complete, Lovastatin is present in the broth in both lactone and acid forms. The open hydroxy acid form of the statins is the biologically active form. However, the statins are generally administered to a patient in the lactone form, which is converted to its active metabolite, the hydroxy acid form, in the body. Thus, since only the lactone form is of commercial interest, the acid form is converted into the lactone form through a process called lactonization. The process of lactonization is an equilibrium reaction whereby the open dihydroxy acid form is converted into the closed lactone form. Because lactonization is an equilibrium process, to obtain a high yield of the lactone product, some means must be employed to shift the equilibrium to the lactone side of the equation. This equilibrium equation can be depicted as follows:

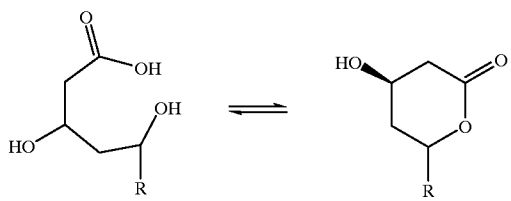

Lactonization is an intramolecular esterification. Intermolecular esterification, which leads to dimer formation and higher oligomeric species competes with lactonization:

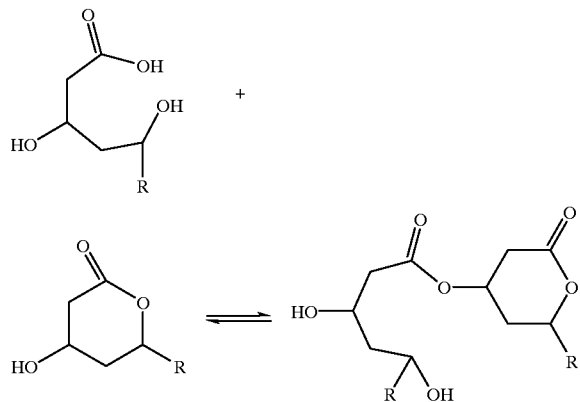

Lactonization methods are known in the art and many such methods are discussed below. Following lactonization of Lovastatin or following synthesis of Simvastatin, the statins are isolated using crystallization techniques known in the art.

Processes known in the literature for the lactonization of the free, hydroxy acid or its salts are either carried out under high temperature conditions, i.e. refluxing with inert solvents, or catalyzed by strong acids when lactonization is effected at ambient temperature. The process disclosed in U.S. Pat. No. 4,820,850 involves heating the free acid or its salts, e.g. the ammonium salt, to reflux temperature (usually 100–110° C.) in high boiling carbohydrate solvents such as toluene for 7–8 hours. The ambient acidity of the acid is believed to be responsible for the lactonization reaction at these high temperatures. In addition, water that is formed as a by-product of the reaction is continuously removed by azeotropic distillation, which forces the reaction to near completion (shifts the position of equilibrium to the lactone side). The process of lactonization under heat conditions of reflux temperatures is complicated by the formation of dimer impurities which lower the quality of the final lactone product. Once formed, the dimer impurity is difficult to remove and is often present at the levels between 0.4 to 0.08% in the product. To minimize dimerization, high dilutions are often used in the lactonization reaction at the cost of the efficiency of the reaction and process, which is disadvantageous on a commercial manufacturing scale.

U.S. Pat. No. 4,916,239 discloses lactonization at room temperature by treating the free ammonium salt of mevinic acid in a mixture of acetic acid and water, and in the presence of a strong acid catalyst. After the free hydroxy acid-lactone equilibrium is established (reaction has proceeded to 50% conversion), water is gradually added in an amount sufficient to effect crystallization of the lactone from the reaction medium. Removal of the lactone from solution favors lactone formation and thus drives the lactonization to completion. Since the lactone is continuously removed from solution, dimer formation is minimized. The disadvantages of this process stem from the inconvenience of using a strong acid catalyst in a large scale synthesis. The strong acid catalysts (e.g. formic, phosphoric, trifluoroacetic, sulphuric, hydrochloric, p-toluene, sulphonic, methanesulphonic acids) that are often used in quantities varying from 1.2 to 1.5 molar equivalents, can be difficult to handle and can pose environmentally unacceptable disposal problems, especially on an industrial scale. Furthermore, the excess acid catalyst that is used requires neutralization by adding a strong base before filtration of the product. Additionally, the lactonization reaction is only about 50% complete after the equilibrium is achieved. Any fast or premature addition of water can lead to serious crystallization and filtration problems. Additionally, reaction and subsequent work-up takes about 9–12 hours for completion, thereby decreasing the efficiency of the process.

U.S. Pat. No. 5,917,058 discloses a process of lactonization which avoids the use of strong corrosive acids and drastic heat conditions. The process involves treating the open hydroxy acid form of statins, preferably in their ammonium salt form, with acetic acid under inert anhydrous conditions at ambient or moderate temperatures. The acetic acid serves both as a solvent and as a catalyst. The lactonization proceeds without the addition of strong acid catalysts. The lactonized product is isolated after completion of reaction by the addition of an anti-solvent that has the ability to crystallize out the lactonized product. The anti-solvents disclosed are water, hexane, heptane, or cyclohexane. Since lactonization is an equilibrium reaction, the reaction by-products—water and ammonia—have to be removed to shift the equilibrium to the lactone side. The acetic acid used in the process consumes, in situ, the ammonia, resulting in the generation of ammonium acetate. The ammonium acetate, since it is hygroscopic in nature, absorbs the other by-product—water. This procedure is reported to yield 85–95% yield with 95–98% purity.

U.S. Pat. No. 5,939,564 also discloses a method of lactonization which avoids the use of strong corrosive acids. The open hydroxy acid in its salt form is heated in an organic solvent at a temperature ranging from ambient to the reflux temperature of the solvent under anhydrous conditions. This mixture is then treated with a mild catalyst at a temperatures ranging from about ambient temperature to about 50° C. The mild catalysts are the salts of organic bases with inorganic or organic acids, such as pyridine hydrobromide, pyridine hydrocholoride, or pyridine p-toluene sulfonate. The lactonized product is then precipitated by the addition of water and finally the crystalline product is collected from the mixture. This method produces at the most, 98.7 % pure Lovastatin.

While the above methods of lactonization have decreased the environmental burden and lead to improved yields and purity, these methods still result in significant formation of dimers of Lovastatin. Additionally, during the synthesis of Simvastatin from Lovastatin, dimer impurities form during lactonization. Thus, there remains a need for a purification process that reduces the level of dimer impurity. The present invention addresses this need.

SUMMARY OF THE INVENTION

It has now been found that dimeric impurities may be removed from Lovastatin or Simvastatin by treatment with mild bases which selectively hydrolyze the dimers without concomitant ring opening of the lactone ring of Simvastatin or Lovastatin.

The preferred mild bases include aliphatic mono- or di- or triamines, aromatic amines, ammonium hydroxide, ammonia gas and an aqueous solution of the above agents.

Using the process of purification of the present invention, Lovastatin or Simvastatin containing less than about 0.08% dimeric impurities can be obtained. Thus, another aspect of the invention provides the compounds, Lovastatin and Simvastatin having less than about 0.08% dimeric impurities.

DETAILED DESCRIPTION OF THE INVENTION

As discussed above, known processes of synthesizing Simvastatin or lactonization of Lovastatin, result in the formation of unwanted dimer impurities. The dimer impurities are hard to remove as they co-crystallize with the Lovastatin and Simvastatin. The present invention provides a process of purification of Lovastatin or Simvastatin, which reduces the level of these dimer impurities. The present invention provides a method of purifying Lovastatin or Simvastatin in substantially pure lactone forms. The process of the present invention produces Lovastatin or Simvastatin having less than about 0.08% dimeric impurities.

The process of the present invention utilizes a slightly alkaline condition in a solvent mixture containing Lovastatin or Simvastatin, to hydrolyze Lovastatin dimer or Simvastatin dimer and other ester-like impurities, without concomitantly opening up the lactone ring. A mild base agent of 0.4 molar equivalent or less is added to the solvent mixture to produce alkaline condition. The preferred mild base agents include aliphatic mono-, di- or triamines, aromatic amines, ammonium hydroxide, ammonia gas and aqueous solutions of the foregoing agents and mixtures thereof. The most preferred mild base agent is ammonium-hydroxide.

The lactone forms of simvastatin or lovastatin (the "statin lactones") substantially differ in their solubility from the hydroxy acid forms and can be separated accordingly. Lovastatin dimer may be hydrolized to lovastatin hydroxy acid, anhydrolovastatin and lovastatin lactone. The observed ratio of anhydrolovastatin:lovastatin depends on the presence of water. The presence of water is limited because it helps the opening of the lactone form. The statin lactones recovered from the solvent mixture. The statin lactones may be recovered by crystallization from an appropriate solvent, using methods known in the art. Crystallization may be performed by cooling the solvent mixture used for hydrolyzing the lactone. Alternatively, the solvent mixture used for hydrolysis may be evaporated and the solid resuspended in a crystallizing solution. Preferred crystallization solvents include isobutyl acetate, ethanol, butylacetate, acetonitrile, mixtures of the afformentioned solvents, mixtures of ethanol-water and mixtures of methanol-water. A preferred solvent mixture is isobutyl acetate:ethanol at a ratio of about 3:1. For crystallization with ethanol and water, a preferred ratio is 0.8:1.1. For crystallization with methanol and water, a preferred ratio is 0.7:1.0. Preferably the crystallization is performed at a temperature of about −20° C. to about +25° C. More preferably the crystallization is performed at a temperature of about −15° C. to about +15° C., and most preferably at about −15° C. to about +5° C.

Another aspect of the present invention is directed to the solvent mixture used to purify the Lovastatin or Simvastatin. In one aspect of the invention, the solvent mixture comprises an alcohol ancl another solvent component or components. The alcohol in the solvent mixture can be any alkyl alcohol, aromatic alcohol, or a mixture of such alcohols. The preferred alcohols include, but are not limited to, methanol, ethanol, i-propanol, n-propanol, i-butanol, n-butanol, t-butanol or mixtures thereof. The most preferred alcohols are methanol and ethanol. A preferred solvent mixture of the present invention comprises an alcohol in an amount from 1–70 v/v %. More preferably the alcohol is present at 5–50 v/v% and most preferably the alcohol is present at 10–30 v/v %.

The other solvent component of the solvent mixture is believed to prevent the hydrolysis or lactone ring opening of Lovastatin and Simvastatin. Preferred solvent components, other than the alcohol of the solvent mixture, include alkane, alkyl-derivative solvents, and ester derivative solvents. Preferred solvents include dichloromethane, dichloroethane, chloroform, carbon tetrachloride, acetonitrile, petroleum ether, heptane, hexane, cyclohexane, acetone, and butyl-methyl keton, methyl acetate, ethyl acetate, propyl acetate, i-butyl acetate, n-butyl acetate, t-butyl acetate, methyl formate, ethyl formate, propyl formate and mixtures thereof. The most preferred solvents are alcohols, such as methanol and ethanol and acetates, such as i-butyl acetate and ethyl acetate.

Another advantage of the present invention is that the solvent mixture dissolves more Lovastatin and Simvastatin than pure solvents and can also be used in the crystallization. Thus, the present method results in increased yield of Lovastatin and Simvastatin in comparison to method previously known in the art.

The process of the present invention results in the production of Lovastatin and Simvastatin containing less than about 0.08% dimeric impurities. Thus, one aspect of the present invention is directed to the compounds of Lovastatin and Simvastatin having less than about 0.08% dimeric impurities.

EXAMPLES

Example 1

100–220 gm of lovastatin (in its lactone forms) are dissolved in one liter solvent mixture of isobutyl acetate:ethanol at a ratio of about 3:1. This mixture is heated at 40–70° C. Concentrated ammonium hydroxide solution at 1.0–2.0% (calculated on the active substance) is added to the solution. This solution is mixed at 40–85° C. for 1–6 hours, then cooled to 20–30° C. in 1–3 hours. The suspension is further cooled at −5 to +10° C. for 2–10 hours. A final cooling at −5 to −20° C. is performed for 15–24 hours. The yield is 90%. HPLC analysis reveals that the Lovastatin dimer is reduced below 0.08 %.

Example 2

100–220 gm of simvastatin (in its lactone forms) are dissolved in one liter solvent mixture of isobutyl acetate:

ethanol at a ratio of about 3:1. This mixture is heated at 40–70° C. Concentrated ammonium-hydroxide solution (0.1–3.0% calculated on the active substance) is added to the solution. This solution is mixed at 40–70° C. for 1–6 hours, then cooled to 20–30° C. in 1–3 hours. The suspension is further cooled at −5 to +10° C. for 2–10 hours. A final cooling at −5 to −20° C. is performed for 15–24 hours. The yield is 90%. HPLC analysis reveals that the simvastatin dimer is reduced below 0.08 %.

Example 3

The process of examples 1 or 2 is performed as above but the solvent mixture is altered as follows. The isobutyl acetate is substituted by one of the following solvents, or a mixture thereof: dichloromethane, dichloroethane, chloroform, carbon tetrachloride, acetonitrile, petroleum ether, heptane, hexane, cyclohexane, acetone, cyclohexanon, butyl-methyl keton, methyl acetate, ethyl acetate, propyl acetate, i-butyl acetate, n-butyl acetate, t-butyl acetate, methyl formate, ethyl formate, propyl formate or another ester. Further, the ethanol is substituted by one of the following alcohols or a mixture thereof: alkyl and aromatic alcohols including methanol, ethanol, i-propanol, n-propanol, i-butanol, n-butanol, t-butanol. The solvent mixture used for hydrolysis is evaporated in vacuum after mixing at 40°–85° C. The solid is dissolved in 20 times ethanol by heating to 50° C. The statin is precipitated by colling to 10°–25° C. and adding of 28 times water. The crystals are filtered and dried.

Example 4

The procedure of examples 1 or 2 is performed with the following modifications: The ammonium hydroxide is substituted with either an aliphatic mono- or di- or triamine, an aromatic amine, or a water solution of the above mentioned amines, or ammonia gas.

Example 5

The procedure of example 1 or 2 is performed, but the alcohol is present at 1–70 v/v % in the solvent mixture. At a 5% ethanol content, the yield is 94%. HPLC analysis reveals that the Lovastatin dimer is below 0.08%.

What is claimed is:

1. A process for reducing the dimeric impurities in Lovastatin or Simvastatin comprising:
   a) dissolving or suspending Lovastatin or Simvastatin containing greater than 0.08% dimeric impurities in a solvent mixture;
   b) treating said solution or suspension with a mild base; and
   c) isolating Lovastatin or Simvastatin containing less than about 0.08% dimeric imputities.

2. The process of claim 1, wherein said mild base is added to said solvent mixture with either stirring of said solvent mixture or mixing said solution.

3. The process of claim 1, further comprising the step of isolating Lovastatin or Simvastatin from said solvent mixture by crystallization.

4. The process of claim 2, wherein said step of stirring or mixing occurs at a temperature from about 5° C. to about the boiling point of said solvent mixture.

5. The process of claim 2, wherein said step of stirring or mixing is carried out for 1 to 10 hours.

6. The process of claim 3, wherein said crystallization is performed at a temperature of about −20° C. to about +25° C.

7. The process of claim 1, wherein the solvent mixture comprises an alcohol and another solvent component.

8. The process of claim 7, wherein the solvent mixture comprises an alcohol in an amount of from about 1 to about 70 v/v %.

9. The process of claim 7, wherein said alcohol is selected from the group consisting of alkanols, aromatic alcohols, or mixture of said alcohols.

10. The process of claim 7, wherein said alcohol is selected from the group consisting of Methanol, Ethanol, i-Propanol, n-Propanol, i-Butanol, n-Butanol, t-Butanol or a mixture thereof.

11. The process of claim 7, wherein said solvent component is selected from the group consisting of esters or a mixture of esters, acetonitrile, a mixture of an ester and further solvent components, a mixture of acetonitrile and further solvent components, a mixture of an ester and acetonitrile, a mixture of esters and acetonitrile, or a mixture of esters and further solvent components.

12. The process of claim 11, wherein the ester is selected from the group consisting of methyl acetate, ethyl acetate, propyl acetate, i-butyl acetate, n-butyl acetate, t-butyl acetate, methyl formate, ethyl formate, and propyl formate and mixtures thereof.

13. The process of claim 11, wherein the solvent component is selected from the group consisting of dichloromethane, dichloroethane, chloroform, carbon tetrachloride, acetonitrile, petroleum ether, heptane, hexane, cyclohexane, acetone, and butyl-methyl keton and mixtures thereof.

14. The process of claim 1, wherein said basic agent is selected from the group consisting of aliphatic mono- or di- or triamines, aromatic amines, ammonium hydroxide, ammonia gas, an aqueous solution of any of the foregoing, and mixtures thereof.

15. Lovastatin containing less than about 0.08% dimeric impurities, produced by the process of claim 1.

16. Simvastatin containing less than about 0.08% dimeric impurities, produced by the process of claim 1.

17. A process for a statin selected from the group consisting of Lovastatin or Simvastatin comprising:
   a) dissolving or suspending the statin in the solvent comprising 1-70% or an alcohol selected from the group consisting of Methanol, Ethanol, i-Propanol, n-Propanol, i-Butanol, n-Butanol, t-Butanol and a mixture thereof; and a second solvent selected from the group dichloromethane, dichloroethane, chloroform, carbon tetrachloride, acetonitrile, petroleum ether, heptane, hexane, cyclohexane, acetone, butyl-methyl keton, methyl acetate, ethyl acetate, propyl acetate, i-butyl acetate, n-butyl acetate, t-butyl acetate, methyl formate, ethyl formate, propyl formate; and a mixture of said solvents;
   b) adding a mild base selected from the group aliphatic mono- or di- or triamines, aromatic amines, ammonium hydroxide, ammonia gas, an aqueous solution of any of the foregoing, and mixtures thereof;
   c) treating of the solution; and
   d) isolating lovastatin or simvastatin from said solvent mixture by crystallization or precipitation, at about −20° C. to about +25° C.

18. Lovastatin containing less than about 0.08% dimeric impurities produced by the process of claim 17.

19. Simvastatin containing less than about 0.08% dimeric impurities produced by the process of claim 17.

* * * * *

UNITED STATES PATENT AND TRADEMARK OFFICE
CERTIFICATE OF CORRECTION

PATENT NO.     : 6,521,762 B2
DATED          : February 18, 2003
INVENTOR(S)    : Vilmos Keri and Ilona Forgas It is certified that error appears in the above-identified patent and that said Letters Patent is hereby corrected as shown below:

<u>Column 8,</u>
Lines 36-39, delete claims 15-16.
Lines 62-65, delete claims 18-19.

Signed and Sealed this

Second Day of September, 2003

JAMES E. ROGAN
*Director of the United States Patent and Trademark Office*